US011636493B2

United States Patent
Thompson et al.

(10) Patent No.: US 11,636,493 B2
(45) Date of Patent: Apr. 25, 2023

(54) SYSTEM AND COMPUTER-IMPLEMENTED METHOD FOR USING LOCATION DATA ON A CARD NETWORK TO DETECT AND ADDRESS BILLING FRAUD

(71) Applicant: Mastercard International Incorporated, Purchase, NY (US)

(72) Inventors: Emily Marie Thompson, St. Peters, MO (US); Christopher Eric Mullen, St. Peters, MO (US); Kyle Leslie, O'Fallon, MO (US); Richard B. Unnerstall, O'Fallon, MO (US); Brian A. Williams, Wentzville, MO (US)

(73) Assignee: Mastercard International Incorporated, Purchase, NY (US)

(*) Notice: Subject to any disclaimer, the term of this patent is extended or adjusted under 35 U.S.C. 154(b) by 462 days.

(21) Appl. No.: 16/741,301

(22) Filed: Jan. 13, 2020

(65) Prior Publication Data

US 2021/0217029 A1 Jul. 15, 2021

(51) Int. Cl.
*G06K 5/00* (2006.01)
*G06Q 30/018* (2023.01)
(Continued)

(52) U.S. Cl.
CPC ......... *G06Q 30/0185* (2013.01); *G06K 7/087* (2013.01); *G06K 7/10366* (2013.01);
(Continued)

(58) Field of Classification Search
CPC .... G16H 70/00; G06K 7/087; G06K 7/10386; G06Q 20/202; G06Q 20/204; G06Q 20/34; G06Q 50/265
(Continued)

(56) References Cited

U.S. PATENT DOCUMENTS 9,727,919 B2 8/2017 Gregg et al.
10,645,072 B2 * 5/2020 Hefetz ................ G06Q 50/265
(Continued)

OTHER PUBLICATIONS

Webpage printout entitled "Prevent Online Fraud" www.digitalelement.com/application/prevent-online-fraud/ (printed May 20, 2019).
(Continued)

*Primary Examiner* — Daniel St. Cyr
(74) *Attorney, Agent, or Firm* — Hovey Williams LLP

(57) ABSTRACT

A system and computer-implemented method for detecting and addressing billing fraud by an asserted provider of a good or service based on location data associated with card-based financial transactions by an asserted recipient and collected, stored, analyzed, and acted on by a payment card network to determine and respond to a likelihood of fraud. A computer stores locations of the recipient based on uses of a payment card over a time period, and determines a location of the provider based on location data associated with a card reader at a particular time at which the good or service was allegedly provided. The computer compares the two locations for the particular time and generates a fraud score based on a likelihood that the recipient was physically capable of being at the provider location at the particular time, and based on the score, may notify the recipient and decline the payment request.

20 Claims, 2 Drawing Sheets

Figure 1:
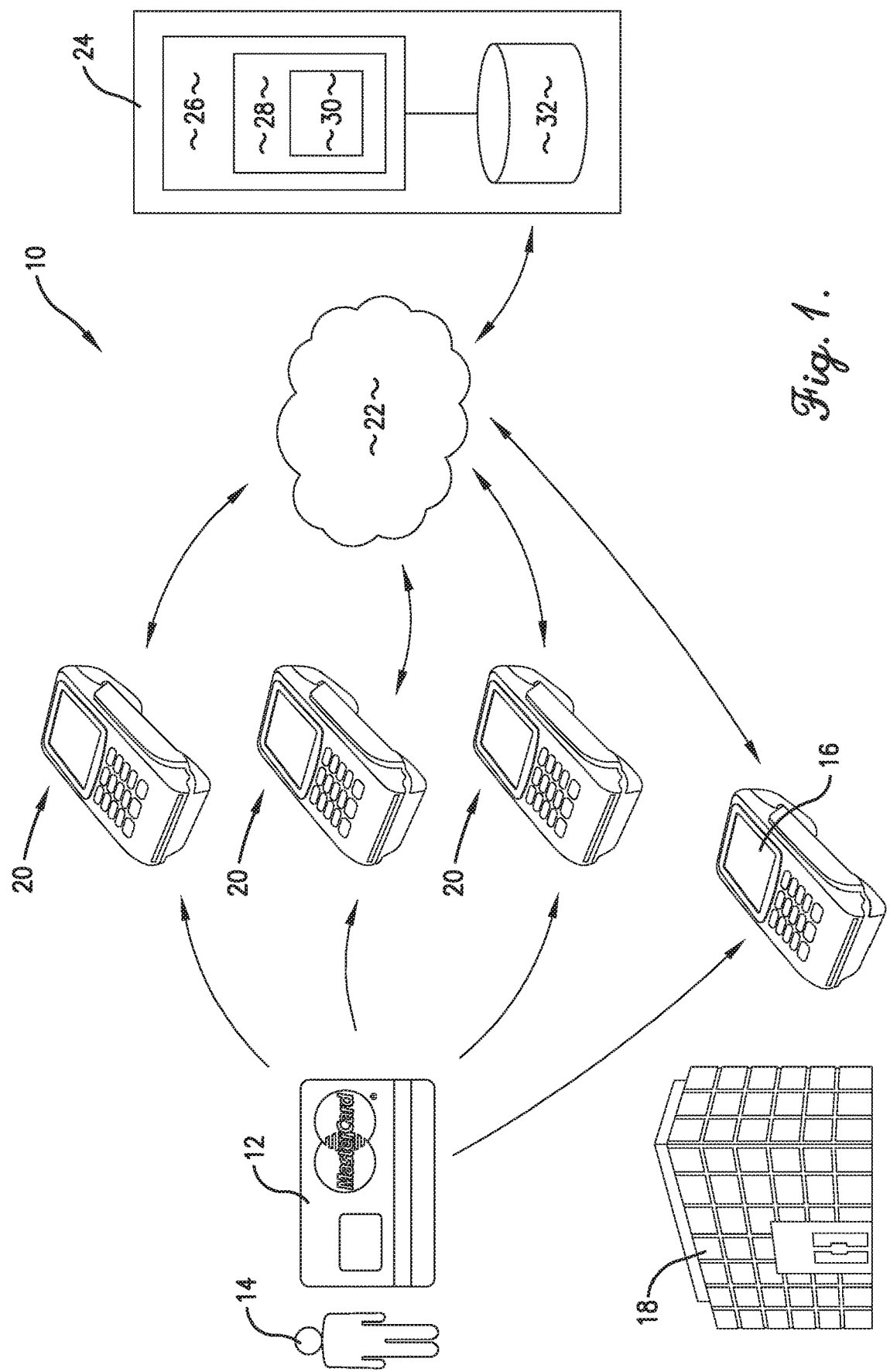

(51) Int. Cl.
  *G06Q 20/34* (2012.01)
  *G06Q 50/26* (2012.01)
  *G06K 7/10* (2006.01)
  *G06Q 20/20* (2012.01)
  *G06K 7/08* (2006.01)
  *G16H 70/00* (2018.01)

(52) U.S. Cl.
  CPC ......... *G06Q 20/202* (2013.01); *G06Q 20/204* (2013.01); *G06Q 20/34* (2013.01); *G06Q 50/265* (2013.01); *G16H 70/00* (2018.01)

(58) Field of Classification Search
  USPC ............. 705/2; 235/380, 382, 383, 487, 492
  See application file for complete search history.

(56) References Cited

U.S. PATENT DOCUMENTS

| | | | |
|---|---|---|---|
| 10,817,879 B2* | 10/2020 | Mossoba | G06Q 20/047 |
| 11,238,455 B1* | 2/2022 | Daniyalzade | G06F 21/577 |
| 11,263,643 B2* | 3/2022 | Huang | G06F 16/2264 |
| 11,270,312 B1* | 3/2022 | Jass | G06Q 20/4016 |
| 2012/0305644 A1 | 12/2012 | Daniels, Jr. | |
| 2017/0011180 A1 | 1/2017 | Andrews et al. | |
| 2017/0373871 A1 | 12/2017 | Breazeale, Jr. | |
| 2020/0334687 A1* | 10/2020 | Ren | G06N 5/003 |

OTHER PUBLICATIONS

Mary Wisniewski "Location Data Could Become Key to Fighting Bank Fraud" American Banker (Aug. 27, 2014).

* cited by examiner

SYSTEM AND COMPUTER-IMPLEMENTED METHOD FOR USING LOCATION DATA ON A CARD NETWORK TO DETECT AND ADDRESS BILLING FRAUD

FIELD

The present invention relates to fraud detection services provided by payment card networks, and more particularly, embodiments concern a system and computer-implemented method for detecting and addressing billing fraud by an asserted provider of a good or service based on location data associated with card-based financial transactions by an asserted recipient and collected, stored, analyzed, and acted on by a payment card network to determine and respond to a likelihood of fraud.

BACKGROUND

Providers of goods and services may commit fraud by billing for goods or services that were not actually provided to asserted recipients. One solution for detecting such fraud is to determine the location of an asserted provider of a good or service, determine the location of an asserted recipient of the good or service at the time they were allegedly provided, and compare the locations to determine whether the asserted recipient was physically capable of receiving the good or service from the asserted provider. If not, then billing fraud may be inferred.

In one example, it is known for an asserted recipient of a good or service to provide evidence (e.g., dated receipts or tickets) that they were out of town or otherwise not physically capable of receiving the good or service from the asserted provider, and thereby prove billing fraud. In another example, for a service that is provided at a recipient's home, it is known to use a dedicated electronic device to determine the location of the asserted provider at the time the service was allegedly provided, and compare the asserted recipient's known home address to the determined location of the asserted provider at that time, and thereby provide evidence that billing fraud did not occur. In yet another example, given a modern smartphone or similarly capable electronic device, it is possible for an asserted recipient of a good or service who regularly tracks their own location to use a record of the tracked location data to provide evidence that they were out of town or otherwise not physically capable of receiving the good or service from the asserted provider, and thereby prove billing fraud. However, all of these different solutions suffer from problems and limitations, including that they place the burden on the asserted recipient to constantly collect, save, and be able to provide evidence of their location, and that they are only used if and when billing fraud is discovered, which may be days, weeks, or months after the fact.

This background discussion is intended to provide information related to the present invention which is not necessarily prior art.

SUMMARY

Embodiments address the above-described and other problems and limitations in the prior art by providing a system and computer-implemented method for detecting and addressing billing fraud by an asserted provider of a good or service based on location data associated with card-based financial transactions by an asserted recipient and collected, stored, analyzed, and acted on by a payment card network to determine and respond to a likelihood of fraud.

In a first embodiment, a system is provided for detecting and addressing billing fraud by an asserted provider of a good or service. The system may include a payment card, a particular card reader device, a plurality of other card reader devices, and a computer on a payment card network. The payment card may be used by an asserted recipient of the good or service and associated with a payment card account managed by the payment card network. The particular card reader device may be used by the asserted provider and configured to read information from the payment card and communicate with the payment card network to make a payment request for the good or service. The other card reader devices may be used by other providers of goods and services and located at other locations relative to the particular card reader device.

The computer of the payment card network may include a processor executing a computer program to perform the following functions. The computer may collect and store one or more recipient locations of the asserted recipient based on one or more transaction locations of one more uses of the payment card by the asserted recipient involving at least one of the other card reader devices over a time period. The computer may determine a provider location of the asserted provider based on location data associated with the particular payment card reader used by the asserted provider to make the payment request at a particular time at which the good or service was allegedly provided. The computer may compare the recipient locations at a closest time within the time period to the particular time at which the good or service was allegedly provided to the provider location at the particular time at which the good or service was allegedly provided. The computer may generate a potential fraud score which reflects a level of certainty based at least in part on a likelihood that the asserted recipient was physically capable of receiving the good or service from the asserted provider at the provider location at the particular time. If the potential fraud score exceeds a pre-established fraud score notification threshold, the computer may notify the asserted recipient of potential billing fraud. If the potential fraud score exceeds a pre-established fraud score declination threshold, the computer may decline the payment request from the asserted provider.

In a second embodiment, a computer-implemented method is provided for improving the functionality of a computer of a payment card network for detecting and addressing billing fraud by an asserted provider of a good or service. The computer-implemented method may include the following steps performed by the computer. The computer may collect and store one or more recipient locations of an asserted recipient of a good or service, the recipient locations being based on one or more transaction locations of one more uses of a payment card by the asserted recipient in one or more financial transactions over a time period. The computer may determine a provider location of an asserted provider of the good or service, the provider location being based on location data associated with a particular payment card reader used by the asserted provider to make a payment request at a particular time at which the good or service was allegedly provided. The computer may compare the recipient locations at a closest time within the time period to the particular time at which the good or service was allegedly provided to the provider location at the particular time at which the good or service was allegedly provided. The computer may generate a potential fraud score which reflects a level of certainty based at least in part on a likelihood that the asserted recipient was physically capable of receiving the good or service from the asserted provider at the provider location at the particular time. If the potential fraud score exceeds a pre-established fraud score notification threshold, the computer may notify the asserted recipient of potential billing fraud. If the potential fraud score exceeds a pre-established fraud score declination threshold, the computer may decline the payment request from the asserted provider.

Various implementations of the foregoing embodiments may include any one or more of the following features. The good or service may be a healthcare good or service as determined by a charge code provided by the particular payment card reader. The location data associated with the particular payment card reader may be a media access control or Internet protocol address. The time period may be from at least twelve hours before the particular time at which the good or service was allegedly provided, or the time period may be from at least twelve hours before to at least twelve hours after the particular time at which the good or service was allegedly provided. The level of certainty may be based at least in part on a physical distance between the recipient location at the closest time and the provider location at the particular time. The level of certainty may be based at least in part on prior billing fraud by the asserted provider. If the potential fraud score exceeds the pre-established fraud score notification threshold, the computer may notify a health insurer associated with the asserted recipient. The computer functions of the system and/or the computer-implemented method for detecting and addressing billing fraud may be implemented for all payment requests to the payment card network, for all payment requests to the payment card network that exceed a pre-established payment request threshold amount, and/or for all payment requests to the payment card network associated with a subset of asserted recipients. The computer functions of the system and/or the computer-implemented method for detecting and addressing billing fraud may be part of a larger fraud detection scheme involving additional data collection and analysis to further refine the potential fraud score.

This summary is not intended to identify essential features of the present invention, and is not intended to be used to limit the scope of the claims. These and other aspects of the present invention are described below in greater detail.

DRAWINGS

Figure 2:
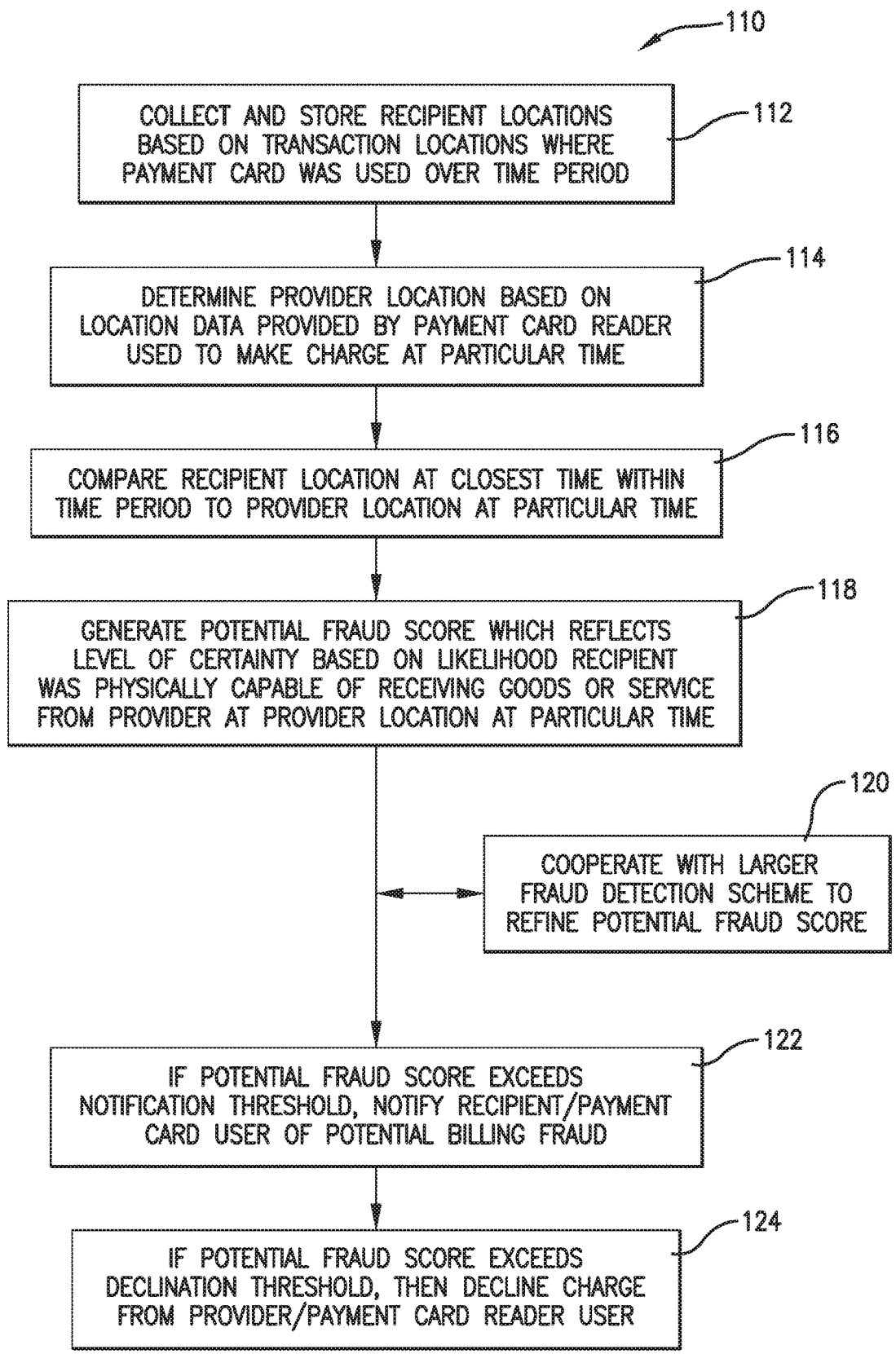

Embodiments of the present invention are described in detail below with reference to the attached drawing figures, wherein:

FIG. 1 is a high-level diagram of an embodiment of a system for detecting and addressing billing fraud by an asserted provider of a good or service based on location data associated with card-based financial transactions by an asserted recipient; and FIG. 2 is a high-level flowchart of an embodiment of a computer-implemented method for detecting and addressing billing fraud by an asserted provider of a good or service based on location data associated with card-based financial transactions by an asserted recipient.

The figures are not intended to limit the present invention to the specific embodiments they depict. The drawings are not necessarily to scale.

DETAILED DESCRIPTION

The following detailed description of embodiments of the invention references the accompanying figures. The embodiments are intended to describe aspects of the invention in sufficient detail to enable those with ordinary skill in the art to practice the invention. The embodiments of the invention are illustrated by way of example and not by way of limitation. Other embodiments may be utilized and changes may be made without departing from the scope of the claims. The following description is, therefore, not limiting. It is contemplated that the invention has general application to processing financial transaction data by a third party in industrial, commercial, and residential applications. The scope of the present invention is defined only by the appended claims, along with the full scope of equivalents to which such claims are entitled.

In this description, references to "one embodiment," "an embodiment," or "embodiments" mean that the feature or features referred to are included in at least one embodiment of the invention. Separate references to "one embodiment," "an embodiment," or "embodiments" in this description do not necessarily refer to the same embodiment and are not mutually exclusive unless so stated. Specifically, a feature, component, action, step, etc. described in one embodiment may also be included in other embodiments, but is not necessarily included. Thus, particular implementations of the present invention can include a variety of combinations and/or integrations of the embodiments described herein.

Broadly characterized, embodiments provide a system and computer-implemented method for detecting and addressing billing fraud by an asserted provider of a good or service based on location data associated with card-based financial transactions by an asserted recipient and collected, stored, analyzed, and acted on by a payment card network to determine and respond to a likelihood of fraud. Embodiments may be particularly useful when the nature of the goods or services is such that they are normally or always provided directly to or otherwise in the physical presence of the asserted recipient, such as is often the case with medical or other healthcare goods or services. It will be understood that embodiments are directed to an improvement in the capability or functionality of a computer, which is particular to a payment card network, to provide a particular solution (i.e., analyzing location data associated with payment card transactions) to a particular problem (i.e., billing fraud) in a particular field (payment card network services, especially billing fraud detection services).

Referring to FIG. 1, an embodiment of a system 10 is shown for detecting and addressing billing fraud by an asserted provider of a good or service based on location data associated with card-based financial transactions by an asserted recipient and collected, stored, analyzed, and acted on by a payment card network to determine and respond to a likelihood of fraud. Broadly, the system 10 may include a payment card 12 associated with an asserted recipient 14 of a good or service; a particular card reader device 16 associated with an asserted provider 18 of the good or service; a plurality of other card reader devices 20; an electronic communication network 22; and a payment card network 24 including a computer 26.

The payment card 12 may be substantially any suitable payment card, such as a credit and/or debit card issued by Mastercard, employing substantially any suitable card technology, such as electronic chip, magnetic stripe, or other technologies. The payment card 12 may be associated with a payment card account managed by the payment card network 24. The asserted recipient 14 of the good or service may be a user of the payment card 12. The particular card reader device 16 may employ substantially any suitable technology for reading information from the payment card 14 and communicating with the payment card network 24 over the electronic communication network 22 to make a payment request for the good or service. The asserted provider 18 of the good or service may be a user of the particular card reader device 16. In one implementation, the asserted provider 18 may have a mobile or fixed location. In one implementation, the good or service may be a medical or other healthcare good or service.

The plurality of other card reader devices 20 may each be located at another location relative to the particular card reader device 16 used by the asserted provider 18 of the good or service, may be used by other providers of goods or services, and may similarly employ substantially any suitable technology for reading information from the payment card 12 and communicating with the payment card network 22 over the electronic communication network 22 to make payment requests for other goods or services. The electronic communication network 22 may be an existing network employing substantially any suitable communication technology (e.g., hardwired, wireless, cellular, Internet). The electronic communication network 22 may carry communication traffic other than communications between the various payment card reader devices 16,20 and the payment card network 24.

The payment card network 22 may be configured to communicate via the electronic communication network 22 with the particular card reader 16 and with the plurality of other card readers 20 to receive and process payment requests, store transaction data (including location data), and confirm or deny payment for each payment request. The computer 26 of the payment card network 22 may include a processor 28 executing a computer program 30 and may include or be in communication with an electronic memory 32 for storing and retrieving data. The computer 26 may function substantially as follows within a larger operational context, and it will be appreciated that such functioning is an improvement in the capability of the computer 26 to detect and address billing fraud.

Referring to FIG. 2, the asserted recipient 14 may travel to one or more transaction locations and engage in one or more uses of the payment card 12 in one or more financial transactions involving payment requests made via the one or more other payment card readers 20 over a time period, and the computer 26 of the payment card network 24 may collect and store the one or more recipient locations (in, e.g., the electronic memory 32), as shown in 112. The good or service may be a medical or other healthcare good or service. If the system 10 is detecting and addressing billing fraud in real-time, then the time period may be from at least twelve hours, or at least twenty-four hours, or at least one week before the particular time at which the good or service was allegedly provided. Alternatively, if the system 10 is detecting and addressing billing fraud not in real-time, then the time period may be from at least twelve hours, or at least twenty-four hours, or at least one week before and after the particular time at which the good or service was allegedly provided.

The asserted provider 18 may make a payment request for a good or service against the asserted recipient's payment card account via the particular payment card reader 16 (which may be fixed or mobile) at a particular time at which the good or service was allegedly provided, and the computer 26 of the payment card network 24 may determine a provider location based on location data (e.g., a media access control (MAC) or Internet protocol (IP) address) associated with the particular payment card reader 16, as shown in 114. The particular payment card reader 16 may provide a charge code identifying the nature of the good or service (as, e.g., a healthcare good or service).

Automatically or upon request, the computer 26 of the payment card network 24 may compare the one or more recipient locations at a closest time within the time period to the particular time at which the good or service was allegedly provided to the provider location at the particular time at which the good or service was allegedly provided, as shown in 116.

Based at least in part on this comparison, the computer 26 of the payment card network 24 may generate a potential fraud score which, quantitively (i.e., a percentage or other number) or qualitatively (i.e., a level in a hierarchical scheme), reflects a level of certainty based at least in part on a likelihood that the asserted recipient was physically capable of receiving the good or service from the asserted provider at the provider location at the particular time, as shown in 118. In one implementation, the level of certainty may be based at least in part on a physical distance between the recipient location at the closest time and the provider location at the particular time. For example, if the intervening physical distance could not possibly be traversed in the time difference, then the level of certainty may be higher than if it reasonably could or definitely could. In one implementation, the level of certainty may be based at least in part on the presence of absence of prior billing fraud by the asserted provider. So, for example, if the asserted provider has previously billed the asserted recipient or other asserted recipients for the good or service with or without fraud complaint to the payment card network from the asserted recipient or other asserted recipients, then the level of certainty is correspondingly higher or lower (i.e., if there is a specific or general history of seemingly fraudulent or non-fraudulent billing, then the level of certainty may be higher if the former and lower if the latter).

In one implementation, the system 10 for detecting and addressing billing fraud may be part of a larger fraud detection scheme involving additional data collection and analysis to further refine the potential fraud score, as shown in 120. The larger fraud scheme may employ known fraud detection solutions or versions thereof.

If the potential fraud score exceeds a pre-established fraud score notification threshold, then the computer 26 of the payment card network 24 may notify the asserted recipient of potential billing fraud, as shown in 122. In one implementation, the computer 26 of the payment card network 24 may also notify a health insurer associated with the asserted recipient. In one implementation in which the potential fraud score is a quantitative percentage, the pre-established fraud score notification threshold may be, for example, at least fifty percent, or at least seventy five percent, or at least ninety percent certainty. In one implementation in which the potential fraud score is a qualitative level in a hierarchical scheme, the pre-established fraud score notification threshold may be, for example, at least a "medium" or at least a "high" level of certainty or an equivalent qualitative characterization of certainty.

If the potential fraud score exceeds a pre-established fraud score declination threshold, then the computer 26 of the payment card network 24 may decline the payment request from the asserted provider, as shown in 124. In one implementation in which the potential fraud score is a quantitative percentage, the pre-established fraud score declination threshold may be, for example, at least fifty percent, or at least seventy five percent, or at least ninety percent certainty. In one implementation in which the potential fraud score is a qualitative level in a hierarchical scheme, the pre-established fraud score declination threshold may be, for example, at least a "medium" or at least a "high" certainty or an equivalent qualitative characterization of certainty. In alternative implementations, the pre-established fraud score notification and declination thresholds may be the same, or the notification threshold may be lower than the declination threshold.

In various implementations, the system 10 for detecting and addressing billing fraud may be implemented for all payment requests to the payment card network 24, for all payment requests to the payment card network 24 that exceed a pre-established payment request threshold amount (e.g., at least one hundred dollars, at least five hundred dollars, or at least one thousand dollars), for all payment requests for one or more particular goods and/or services (e.g., medical or other healthcare goods or services) which are identifiable by charge codes provided by card readers when making the payment requests, or for all payment requests to the payment card network 24 associated with a subset of asserted recipients (e.g., enrollees or frequent recipients of such goods and/or services).

The system 10 may include more, fewer, or alternative components and/or perform more, fewer, or alternative actions, including those discussed elsewhere herein, and particularly those discussed in the following section describing the computer-implemented method 110.

Referring again to FIG. 2, an embodiment of a computer-implemented method 110 is shown for detecting and addressing billing fraud by an asserted provider of a good or service based on location data associated with card-based financial transactions by an asserted recipient and collected, stored, analyzed, and acted on by a payment card network to determine and respond to a likelihood of fraud. Broadly, the computer-implemented method 110 may include the following steps which may be implemented by the computer 26 of the payment card network 24 of the above-described system 10. It will be appreciated that the computer-implemented method 110 improves the capability or functioning of the computer 26 to detect and address billing fraud.

A computer 26 of a payment card network 24 may collect and store (in, e.g., an electronic memory 32) one or more recipient locations of an asserted recipient of a good or service, with the recipient locations being based on one or more transaction locations of one more uses of a payment card 12 by the asserted recipient 14 in one or more financial transactions over a time period, as shown in 112. The good or service may be a medical or other healthcare good or service. If the computer-implemented method 110 is detecting and addressing billing fraud in real-time, then the time period may be from at least twelve hours, or at least twenty-four hours, or at least one week before the particular time at which the good or service was allegedly provided. Alternatively, if the computer-implemented 110 is detecting and addressing billing fraud not in real-time, then the time period may be from at least twelve hours, or at least twenty-four hours, or at least one week before and after the particular time at which the good or service was allegedly provided.

The computer 26 of the payment card network 24 may determine a provider location of an asserted provider of the good or service, with the provider location being based on location data (e.g., a MAC/IP address) associated with a particular payment card reader 16 (which may be fixed or mobile) used by the asserted provider to make a payment request at a particular time at which the good or service was allegedly provided, as shown in 114. The particular payment card reader 16 may provide a charge code identifying the nature of the good or service (as, e.g., a healthcare good or service).

Automatically or upon request, the computer 26 of the payment card network 24 may compare the one or more recipient locations at a closest time within the time period to the particular time at which the good or service was allegedly provided to the provider location at the particular time at which the good or service was allegedly provided, as shown in 116.

Based at least in part on this comparison, the computer 26 of the payment card network 24 may generate a potential fraud score which, quantitively (i.e., a percentage or other number) or qualitatively (i.e., a level in a hierarchical scheme), reflects a level of certainty based at least in part on a likelihood that the asserted recipient was physically capable of receiving the good or service from the asserted provider at the provider location at the particular time, as shown in 118. In one implementation, the level of certainty may be based at least in part on a physical distance between the recipient location at the closest time and the provider location at the particular time. For example, if the intervening physical distance could not possibly be traversed in the time difference, then the level of certainty may be higher than if it reasonably could or definitely could. In one implementation, the level of certainty is based at least in part on the presence of absence of prior billing fraud by the asserted provider. So, for example, if the asserted provider has previously billed the asserted recipient or other asserted recipients for the good or service with or without fraud complaint to the payment card network from the asserted recipient or other asserted recipients, then the level of certainty is correspondingly higher or lower (i.e., if there is a specific or general history of seemingly fraudulent or non-fraudulent billing, then the level of certainty may be higher if the former and lower if the latter).

In one implementation, the computer-implemented method 110 for detecting and addressing billing fraud may be part of a larger fraud detection scheme involving additional data collection and analysis to further refine the potential fraud score, as shown in 120. The larger fraud scheme may employ known fraud detection solutions or versions thereof.

If the potential fraud score exceeds a pre-established fraud score notification threshold, then the computer 26 of the payment card network 24 may notify the asserted recipient of potential billing fraud, as shown in 122. In one implementation, the computer 24 of the payment card network 26 may also notify a health insurer associated with the asserted recipient. In one implementation in which the potential fraud score is a quantitative percentage, the pre-established fraud score notification threshold may be, for example, at least fifty percent, or at least seventy five percent, or at least ninety percent certainty. In one implementation in which the potential fraud score is a qualitative level in a hierarchical scheme, the pre-established fraud score notification threshold may be, for example, at least a "medium" or at least a "high" certainty or an equivalent qualitative characterization of certainty.

If the potential fraud score exceeds a pre-established fraud score declination threshold, then the computer 26 of the payment card network 24 may decline the payment request from the asserted provider, as shown in 124. In one implementation in which the potential fraud score is a quantitative percentage, the pre-established fraud score declination threshold may be, for example, at least fifty percent, or at least seventy five percent, or at least ninety percent certainty.

In one implementation in which the potential fraud score is a qualitative level in a hierarchical scheme, the pre-established fraud score declination threshold may be, for example, at least a "medium" or at least a "high" certainty or an equivalent qualitative characterization of certainty. In alternative implementations, the pre-established fraud score notification and declination thresholds may be the same, or the notification threshold may be lower than the declination threshold.

In various implementations, the computer-implemented method 110 for detecting and addressing billing fraud may be implemented for all payment requests to the payment card network 24, for all payment requests to the payment card network 24 that exceed a pre-established payment request threshold amount (e.g., at least one hundred dollars, at least five hundred dollars, or at least one thousand dollars), for all payment requests for one or more particular goods and/or services (e.g., medical or other healthcare goods or services) which are identifiable by charge codes provided by card readers when making the payment requests, or for all payment requests to the payment card network 24 associated with a subset of asserted recipients (e.g., enrollees or frequent recipients of such goods and/or services).

The computer-implemented method 110 may include more, fewer, or alternative actions, including those discussed elsewhere herein and particularly those discussed in the preceding section describing the system 10.

Any actions, functions, steps, and the like recited herein may be performed in the order shown in the figures and/or described above, or may be performed in a different order. Furthermore, some steps may be performed concurrently as opposed to sequentially. Although the computer-implemented method is described above, for the purpose of illustration, as being executed by an exemplary system and/or exemplary physical elements, it will be understood that the performance of any one or more of such actions may be differently distributed without departing from the spirit of the present invention.

A computer-readable medium comprising a non-transitory medium may include an executable computer program stored thereon and for instructing one or more processing elements to perform some or all of the steps described herein, including some or all of the steps of the computer-implemented method. The computer program stored on the computer-readable medium may instruct the processing element and/or other components of the system to perform additional, fewer, or alternative actions, including those discussed elsewhere herein.

All terms used herein are to be broadly interpreted unless otherwise stated. For example, the term "payment card" and the like may, unless otherwise stated, broadly refer to substantially any suitable transaction card, such as a credit card, a debit card, a prepaid card, a charge card, a membership card, a promotional card, a frequent flyer card, an identification card, a prepaid card, a gift card, and/or any other device that may hold payment account information, such as mobile phones, Smartphones, personal digital assistants (PDAs), key fobs, and/or computers. Each type of transaction card can be used as a method of payment for performing a transaction.

The terms "processing element," "processor," and the like, as used herein, may, unless otherwise stated, broadly refer to any programmable system including systems using central processing units, microprocessors, microcontrollers, reduced instruction set circuits (RISC), application specific integrated circuits (ASIC), logic circuits, and any other circuit or processor capable of executing the functions described herein. The above examples are example only, and are thus not intended to limit in any way the definition and/or meaning of the term "processing element." In particular, "a processing element" may include one or more processing elements individually or collectively performing the described functions. In addition, the terms "software," "computer program," and the like, may, unless otherwise stated, broadly refer to any executable code stored in memory for execution on mobile devices, clusters, personal computers, workstations, clients, servers, and a processor or wherein the memory includes read-only memory (ROM), electronic programmable read-only memory (EPROM), random access memory (RAM), erasable electronic programmable read-only memory (EEPROM), and non-volatile RAM (NVRAM) memory. The above memory types are exemplary only, and are thus not limiting as to the types of memory usable for storage of a computer program.

The terms "computer," "computing device," and the like, as used herein, may, unless otherwise stated, broadly refer to substantially any suitable technology for processing information, including executing software, and may not be limited to integrated circuits referred to in the art as a computer, but may broadly refer to a microcontroller, a microcomputer, a programmable logic controller (PLC), an application specific integrated circuit, and other programmable circuits, and these terms are used interchangeably herein.

The term "communication network" and the like, as used herein, may, unless otherwise stated, broadly refer to substantially any suitable technology for facilitating communication (e.g., GSM, CDMA, TDMA, WCDMA, LTE, EDGE, OFDM, GPRS, EV-DO, UWB, WiFi, IEEE 802 including Ethernet, WiMAX, and/or others), including supporting various local area networks (LANs), personal area networks (PAN), or short range communication protocols.

The term "memory element," "data storage device," and the like, as used herein, may, unless otherwise stated, broadly refer to substantially any suitable technology for storing information, and may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others.

Although the invention has been described with reference to the one or more embodiments illustrated in the figures, it is understood that equivalents may be employed and substitutions made herein without departing from the scope of the invention as recited in the claims.

Having thus described one or more embodiments of the invention, what is claimed as new and desired to be protected by Letters Patent includes the following:

1. A system for detecting and addressing billing fraud by an asserted provider of a good or service, the system comprising:
   a payment card used by an asserted recipient of the good or service and associated with a payment card account managed by a payment card network;
   a particular card reader device used by the asserted provider and located at a particular card reader device location and configured to read information from the payment card and communicate with the payment card network to make a payment request for the good or service, the payment request including a particular electronic identifier of the particular card reader device which identifies the particular card reader device location to the payment card network;
a plurality of other card reader devices used by other providers of goods and services and located at other card reader device locations relative to the particular card reader device location, and each other card reader device of the plurality of other card reader devices is associated with a different electronic identifier which identifies the other card reader device location to the payment card network; and
a computer of the payment card network, the computer including a processor executing a computer program to perform functions including—
collect and store one or more of the other card reader device locations associated with one more uses of the payment card by the asserted recipient over a time period, the payment card network determining each other card reader device location of the one or more of the other card reader device locations based on the different electronic identifier provided by each other card reader device of the plurality of other card reader devices to the payment network,
determine the particular card reader device location of the particular payment card reader used by the asserted provider to make the payment request at a particular time at which the good or service was allegedly provided, the payment card network determining the particular card reader device location based on the particular electronic identifier included in the payment request,
compare the other card reader device locations associated with the one more uses of the payment card by the asserted recipient within the time period to the particular time at which the good or service was allegedly provided to the particular card reader device location at the particular time at which the good or service was allegedly provided,
generate a potential fraud score which reflects a level of certainty based at least in part on a likelihood that the asserted recipient was physically capable of receiving the good or service from the asserted provider at the at the particular time,
if the potential fraud score exceeds a pre-established fraud score notification threshold, notify the asserted recipient of potential billing fraud, and
if the potential fraud score exceeds a pre-established fraud score declination threshold, decline the payment request from the asserted provider.

2. The system of claim 1, wherein the particular card reader device location associated with the particular card reader is based on a media access control or Internet protocol address of the particular card reader.

3. The system of claim 1, wherein the time period is from at least twelve hours before the particular time at which the good or service was allegedly provided.

4. The system of claim 1, wherein the time period is from at least twelve hours before to at least twelve hours after the particular time at which the good or service was allegedly provided.

5. The system of claim 1, wherein the level of certainty is based at least in part on a physical distance between the other card reader device locations particular card reader device location at the particular time.

6. A computer-implemented method for improving the functionality of a computer of a payment card network for detecting and addressing billing fraud by an asserted provider of a good or service, the computer-implemented method comprising:
collecting and storing on the computer of the payment card network one or more other card reader device locations associated with one more uses of a payment card by the asserted recipient in one or more financial transactions over a time period, wherein each other card reader device of the plurality of other card reader devices is associated with a different electronic identifier which identifies the other card reader device location to the computer of the payment card network and the computer of the payment card network determines each other card reader device location of the one or more of the other card reader device locations based on the different electronic identifier provided by each other card reader device of the plurality of other card reader devices to the payment network;
determining by the computer of the payment card network a particular card reader device location of a particular payment card reader used by the asserted provider to make a payment request at a particular time at which the good or service was allegedly provided, wherein the payment request includes a particular electronic identifier of the particular card reader device which identifies the particular card reader device location to the computer of the payment card network and the computer of the payment card network determines the particular card reader device location based on the particular electronic identifier included in the payment request;
comparing by the computer of the payment card network the other card reader device locations associated with one more uses of the payment card by the asserted recipient within the time period to the particular time at which the good or service was allegedly provided to the particular card reader device location at the particular time at which the good or service was allegedly provided;
generating by the computer of the payment card network a potential fraud score which reflects a level of certainty based at least in part on a likelihood that the asserted recipient was physically capable of receiving the good or service from the asserted provider at the particular time;
if the potential fraud score exceeds a pre-established fraud score notification threshold, notifying by the computer of the payment card network the asserted recipient of potential billing fraud; and
if the potential fraud score exceeds a pre-established fraud score declination threshold, declining by the computer of the payment card network the payment request from the asserted provider.

7. The computer-implemented method of claim 6, wherein the good or service is a healthcare good or services as determined by a charge code provided by the particular payment card reader.

8. The computer-implemented method of claim 6, wherein the particular card reader device location associated with the particular card reader is based on a media access control or Internet protocol address of the particular card reader.

9. The computer-implemented method of claim 6, wherein the time period is from at least twelve hours before the particular time at which the good or service was allegedly provided.

10. The computer-implemented method of claim 6, wherein the time period is from at least twelve hours before to at least twelve hours after the particular time at which the good or service was allegedly provided.

11. The computer-implemented method of claim 6, wherein the level of certainty is based at least in part on a physical distance between the other card reader device locations and the particular card reader device location at the particular time.

12. The computer-implemented method of claim 6, wherein the level of certainty is based at least in part on prior billing fraud by the asserted provider.

13. The computer-implemented method of claim 6, further including if the potential fraud score exceeds the pre-established fraud score notification threshold, notifying by the computer of the payment card network a health insurer associated with the asserted recipient.

14. The computer-implemented method of claim 6, wherein the computer-implemented method for detecting and addressing billing fraud is implemented for all payment requests to the payment card network.

15. The computer-implemented method of claim 6, wherein the computer-implemented method for detecting and addressing billing fraud is implemented for all payment requests to the payment card network that exceed a pre-established payment request threshold amount.

16. The computer-implemented method of claim 6, wherein the computer-implemented method for detecting and addressing billing fraud is implemented for all payment requests to the payment card network associated with a subset of asserted recipients.

17. The computer-implemented method of claim 6, wherein the computer-implemented method for detecting and addressing billing fraud is part of a larger fraud detection scheme involving additional data collection and analysis to further refine the potential fraud score.

18. A computer-implemented method for improving the functionality of a computer of a payment card network detecting and addressing billing fraud by an asserted provider of a healthcare good or service, the computer-implemented method comprising:
 collecting and storing on the computer of the payment card network one or more other card reader device locations associated with one more uses of a payment card by the asserted recipient in one or more financial transactions over a time period, wherein each other card reader device of the plurality of other card reader devices is associated with a different electronic identifier which identifies the other card reader device location to the computer of the payment card network and the computer of the payment card network determines each other card reader device location of the one or more of the other card reader device locations based on the different electronic identifier provided by each other card reader device of the plurality of other card reader devices to the payment network;
 determining by the computer of the payment card network a particular card reader device location of a particular payment card reader used by the asserted provider to make a payment request at a particular time at which the good or service was allegedly provided, wherein the payment request includes a particular electronic identifier of the particular card reader device which identifies the particular card reader device location to the computer of the payment card network and the computer of the payment card network determines the particular card reader device location based on the particular electronic identifier included in the payment request, and the particular payment card reader providing to the computer of the payment card network a charge code identifying the healthcare good or service as a healthcare good or service;
 comparing by the computer of the payment card network the other card reader device locations associated with one more uses of the payment card by the asserted recipient at a closest time to the particular time at which the healthcare good or service was allegedly provided to the particular card reader device location at the particular time at which the healthcare good or service was allegedly provided;
 generating by the computer of the payment card network a potential fraud score which reflects a level of certainty based at least in part on a physical distance between the recipient location at the closest time and the provider location at the particular time and a likelihood that the asserted recipient was physically capable of receiving the healthcare good or service from the asserted provider at the particular time;
 if the potential fraud score exceeds a pre-established fraud score notification threshold, notifying by the computer of the payment card network the asserted recipient of potential billing fraud; and
 if the potential fraud score exceeds a pre-established fraud score declination threshold, declining by the computer of the payment card network the payment request from the asserted provider.

19. The computer-implemented method of claim 18, wherein the particular card reader device location associated with the particular card reader is based on a media access control or Internet protocol address of the particular card reader.

20. The computer-implemented method of claim 18, wherein the time period is from at least twelve hours before the particular time at which the healthcare good or service was allegedly provided.

* * * * *